(12) United States Patent
Ferguson

(10) Patent No.: US 10,441,378 B2
(45) Date of Patent: *Oct. 15, 2019

(54) MEDICAL HEADLAMP OPTICAL ARRANGEMENT

(71) Applicant: RIVERPOINT MEDICAL, LLC, Portland, OR (US)

(72) Inventor: John Thomas Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/601,061

(22) Filed: May 22, 2017

(65) Prior Publication Data

US 2017/0252122 A1 Sep. 7, 2017

Related U.S. Application Data

(63) Continuation of application No. 13/972,446, filed on Aug. 21, 2013, now Pat. No. 9,687,314.

(Continued)

(51) Int. Cl.
*A61B 90/35* (2016.01)
*F21V 21/084* (2006.01)
(Continued)

(52) U.S. Cl.
CPC ............ *A61B 90/35* (2016.02); *A61B 1/0692* (2013.01); *A61B 90/30* (2016.02); *B29C 70/72* (2013.01);
(Continued)

(58) Field of Classification Search
CPC ... A61B 1/06; A61B 1/0692; A61B 2090/309; A61B 2090/502; A61B 90/30;
(Continued)

(56) References Cited

U.S. PATENT DOCUMENTS

| 3,704,928 A | 12/1972 | Coombs et al. |
| D228,474 S | 9/1973 | Barber |

(Continued)

FOREIGN PATENT DOCUMENTS

| EP | 2479489 A2 | 7/2012 |
| KR | 1020110095674 A1 | 8/2011 |

(Continued)

OTHER PUBLICATIONS medLED, medLED Sapphire O.R. Surgical Headlight System, brochure, medLED//Portable Surgical Lighting, Portland, Oregon United States of America.

*Primary Examiner* — Zheng Song
(74) *Attorney, Agent, or Firm* — Timothy E. Siegel Patent Law, PLLC; Timothy E. Siegel

(57) ABSTRACT

A lamp having a front surface from which light is emitted and that includes a high efficiency light source assembly producing a beam having a 3 dB beamwidth of greater than 100°, and which includes a substrate, a high efficiency light source supported by the substrate; and a dome-lens that contains the high efficiency light source. Also, an optical assembly is positioned to receive light from the light emitting diode assembly and to produce a headlamp light beam emitted from the front surface of the lamp. Further, an annular light block defines an annulus and is placed about the lens, so that the lens protrudes through the annulus, thereby creating a sharp boundary for the output light beam.

7 Claims, 6 Drawing Sheets

Related U.S. Application Data

(60) Provisional application No. 61/822,493, filed on May 13, 2013.

(51) Int. Cl.
   *F21V 5/04*      (2006.01)
   *B29C 70/72*     (2006.01)
   *A61B 1/06*      (2006.01)
   *A61B 90/30*     (2016.01)
   *F21W 131/20*    (2006.01)
   *A61B 90/50*     (2016.01)

(52) U.S. Cl.
   CPC .............. *F21V 5/04* (2013.01); *F21V 21/084* (2013.01); *A61B 2090/309* (2016.02); *A61B 2090/502* (2016.02); *F21W 2131/20* (2013.01)

(58) Field of Classification Search
   CPC ......... A61B 90/35; F21V 21/084; F21V 5/04; F21W 2131/20
   See application file for complete search history.

(56) References Cited

U.S. PATENT DOCUMENTS

| | | | |
|---|---|---|---|
| 5,068,771 A | 11/1991 | Savage, Jr. | |
| 5,400,229 A * | 3/1995 | Lin .......................... | F21K 9/00 362/249.02 |
| 5,667,291 A | 9/1997 | Caplan et al. | |
| 5,769,523 A | 6/1998 | Feinbloom | |
| 5,774,271 A | 6/1998 | Lagerway et al. | |
| 5,926,320 A | 7/1999 | Parkyn, Jr. et al. | |
| 6,033,087 A | 3/2000 | Shozo et al. | |
| 6,464,383 B1 | 10/2002 | Northington et al. | |
| 6,601,966 B1 | 8/2003 | Wiklund et al. | |
| RE39,162 E | 7/2006 | Caplan et al. | |
| 7,210,810 B1 | 5/2007 | Iversen et al. | |
| 7,226,185 B2 | 6/2007 | Dolgin et al. | |
| 7,737,194 B2 | 6/2010 | Kashiwagi et al. | |
| 7,847,302 B2 | 12/2010 | Basin et al. | |
| 9,091,428 B2 | 7/2015 | Ferguson | |
| 9,234,653 B2 | 1/2016 | Ferguson | |
| 9,351,799 B2 | 5/2016 | Ferguson | |
| 9,568,177 B2 | 2/2017 | Ferguson | |
| 9,687,314 B2 | 6/2017 | Ferguson | |
| 9,707,707 B2 | 7/2017 | Ferguson | |
| 2004/0032728 A1* | 2/2004 | Galli ...................... | H01L 33/60 362/84 |
| 2005/0057917 A1* | 3/2005 | Yatsuda ................ | H01L 33/507 362/84 |
| 2005/0099824 A1 | 5/2005 | Dowling et al. | |
| 2005/0117327 A1 | 6/2005 | Gupta | |
| 2005/0243558 A1 | 11/2005 | Van Duyn | |
| 2006/0285316 A1 | 12/2006 | Tufenkjian et al. | |
| 2007/0097703 A1 | 5/2007 | Goldfain | |
| 2008/0144306 A1 | 6/2008 | Medinis | |
| 2008/0316733 A1 | 12/2008 | Spartano et al. | |
| 2009/0161348 A1 | 6/2009 | Spartano et al. | |
| 2009/0168414 A1 | 7/2009 | Baiey | |
| 2009/0207617 A1 | 8/2009 | Merchant et al. | |
| 2010/0091491 A1 | 4/2010 | Jiang et al. | |
| 2010/0110695 A1 | 5/2010 | Nakamura | |
| 2010/0276711 A1* | 11/2010 | Hand .................... | H05K 3/284 257/98 |
| 2011/0026258 A1 | 2/2011 | Chang | |
| 2012/0014113 A1 | 1/2012 | Chen | |
| 2012/0120635 A1 | 5/2012 | Strong et al. | |
| 2013/0101953 A1 | 4/2013 | Stone | |
| 2013/0128586 A1 | 5/2013 | Lim et al. | |
| 2013/0197317 A1 | 8/2013 | Daniel et al. | |
| 2013/0328074 A1 | 12/2013 | Lowes et al. | |
| 2014/0085900 A1 | 3/2014 | Johnson | |
| 2014/0291715 A1 | 10/2014 | Reiherzer et al. | |
| 2014/0334132 A1 | 11/2014 | Ferguson | |
| 2014/0334157 A1 | 11/2014 | Ferguson | |
| 2016/0123563 A1 | 5/2016 | Ferguson | |

FOREIGN PATENT DOCUMENTS

| | | |
|---|---|---|
| WO | 2009063224 A2 | 5/2009 |
| WO | 2010144426 A1 | 12/2010 |

* cited by examiner

MEDICAL HEADLAMP OPTICAL ARRANGEMENT

RELATED APPLICATIONS

This application is a continuation of U.S. patent application Ser. No. 13/972,446 filed on Aug. 21, 2013, which in turns claims benefit of provisional application Ser. No. 61/822,493, filed May 13, 2013, both of which are incorporated by reference as if fully set forth herein.

BACKGROUND

A medical headlamp assembly is a critical part of the surgeon's suite of tools, as it is of great importance that a surgeon can clearly see in the operating theater. The ideal headlamp would be easily portable, light and comfortable to wear for at least four hours. Further, it would have battery power, mounted on the headstrap, sufficient to last four hours from one charge, thereby eliminating the necessity of waist mounted battery pack and cables connecting this pack to the lamp, which are uncomfortable and complicate antiseptic protocol. Further the ideal headlamp assembly would create a bright beam of light that was homogenous and uniform in brightness and color, from edge-to-edge, directly along the surgeon's line of sight, without obscuring his or her line of sight. Also, it would be entirely silent, easily adjustable in position and would not be susceptible to infection by mold or any other sort of organism.

Unfortunately, these criteria are not only difficult to meet, but are also frequently at odds with each other. For example, although it is better to have a bright light, this creates more heat, which must be safely expressed from the lamp. It is helpful in the elimination of heat to make the lamp bigger, but doing so is likely to cause it to obscure the surgeon's line of sight and add unbearable weight. Another option for expressing heat would be to provide a fan, but this creates a sound which may be difficult for the surgeon to tolerate. To permit longer battery life it would be helpful to have higher capacity batteries, but doing so makes the assembly heavier and more difficult for the surgeon to tolerate for a long period of time. The batteries could be placed in a waist pack, but doing so requires an electrical line extending from an aseptic area, about the waist underneath the scrubs (anything under the neck is a "sterile" area), to a non-sterile area, on the surgeon's head. This arrangement complicates aseptic protocol.

There is a currently available headlamp assembly that mounts batteries on the headband and that has batteries that can be swapped out, one at a time, for extended surgical periods. The light produced by this headlamp is on the order of 166 lumens in intensity. For many types of surgery, for example where a deep cavity that has been opened up inside a patient requires illumination, a higher intensity lamp is desirable.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention takes the form of a lamp having a front surface from which light is emitted and that includes a high efficiency light source assembly producing a beam having a 3 dB beamwidth of greater than 100°, and which includes a substrate, a high efficiency light source supported by the substrate; and a dome-lens that contains the high efficiency light source. Also, an optical assembly is positioned to receive light from the light emitting diode assembly and produce a headlamp light beam emitted from the front surface of the lamp. Further, an annular light block defines an annulus and is placed about the lens, so that the lens protrudes through the annulus, thereby creating a sharp boundary for the output light beam.

In a second separate aspect, the present invention takes the form of a lamp having a light source and an annular light block positioned to block an annulus of the light produced by the light source, the annular light block being thinner than 75μ.

In a third separate aspect, the present invention takes the form of a lamp having a front surface from which a beam of light is emitted and that includes a housing, and a high efficiency light source assembly, having a high efficiency light source covered by a lens, supported within the housing, an optical assembly, supported by the housing and having a front surface that is coincident with the front surface of the lamp and positioned to accept light from the high efficiency light source assembly and to emit the light from the front surface, and having a rear surface that defines a concavity; and wherein the high efficiency light source lens protrudes into the concavity.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Definitions

For the purposes of this application, a "high efficiency light source" is an electrically powered light source having a light emitting surface area of less than 50 mm$^2$ that produces light at a rate of greater than 50 lumens per watt of input power and at a rate greater than 30 lumens per square millimeter of light emitting area. This term does not include packaging or a lens. If these items are included the phrase used is "high efficiency light source assembly".

A light emitting diode (LED), as used in the application, refers to a solid state electrical device and does not include any lens or packaging. This element is sometimes referred to as a "die," by others. A light emitting diode assembly, includes packaging and a lens.

The term "most" as used in this application, means more than 50%.

The term "light" as used in this application refers to visible light.

The "front" of the medical lamp is the side from which light is emitted. The "longitudinal dimension" extends from front to back.

Figure 1:
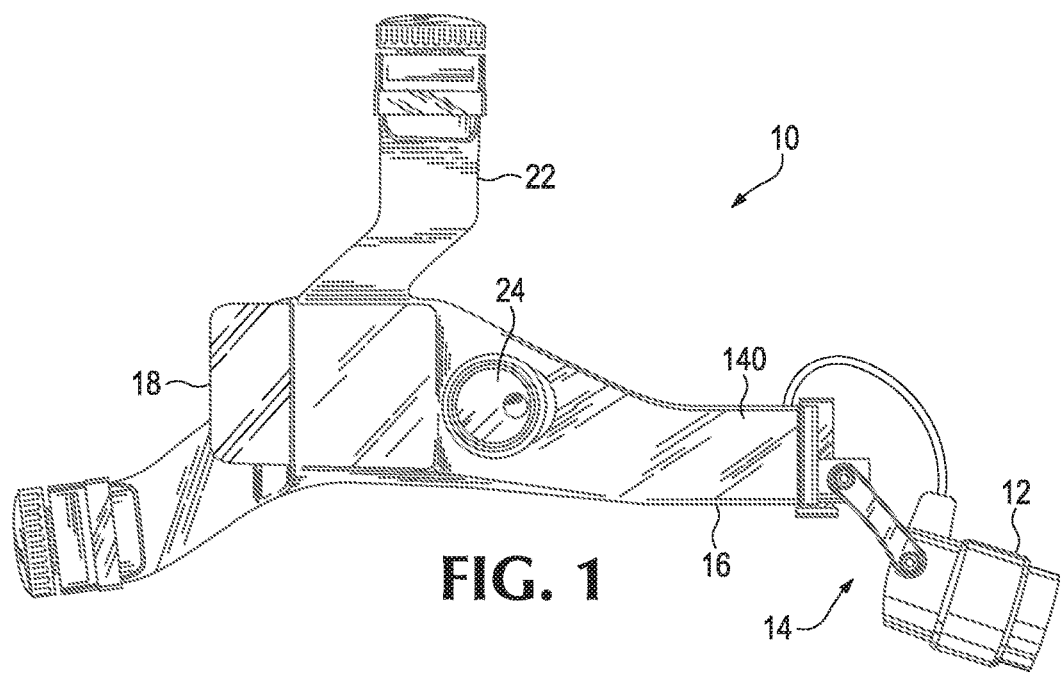
FIG. 1 shows a side view of a medical headlamp assembly, according to the present invention.
Figure 2:
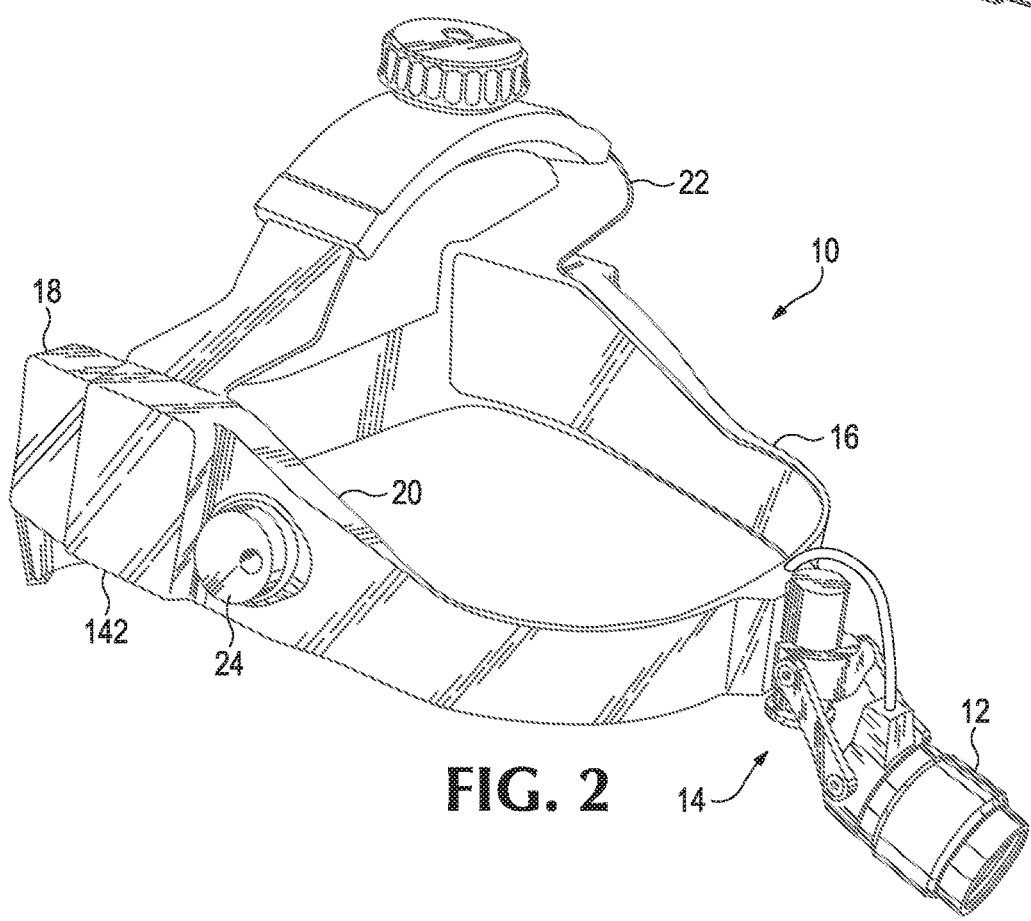
FIG. 2 shows an isometric view of the medical headlamp assembly of FIG. 1.

Referring to FIGS. 1 and 2, in a preferred embodiment of the present invention is a medical headlamp assembly 10, having a headlamp optical assembly (bezel) 12, an adjustable headlamp bezel support assembly 14, a headstrap assembly 16, supporting a pair of batteries 18, each in contact to a circuit board (not shown) in a circuit board repository 20. A head-top strap 22 and brightness control knob 24 also are supported by headstrap assembly 16. Assembly 10 includes a headlamp bezel 12 that has a slightly larger diameter than generally found in the prior art. This permits a brighter light beam since it can support more power intake (drive current), as the greater surface area permits more heat to be radiated away. But it also necessitates a better degree of positioning control and ease of positioning control.

It is highly desirable, but very difficult, to produce a large, clear, sharp round light spot for a surgeon, using LED technology that is powered by head-mounted batteries. To do this it would be beneficial to use an LED assembly that produces a cone of light having a 3 dB beam width of greater than 90°, but there is no such LED assembly available that produces a beam that has a sharp edge while still being efficient enough to provide the brightness necessary to do a deep cavity surgery. The Oslon Square™ LED assembly provides a beam width of 120°, and although bright enough was considered unusable in this application due to the slow tapering off of the beam edges, which if not corrected would create a spot of light having a fuzzy boundary, when an aspheric lens system is used, as is typical. This detracts from the tight focus on a specific area that the medical light is intended to provide and can cause distracting reflections of the metal instruments used in surgery.

Figure 3:
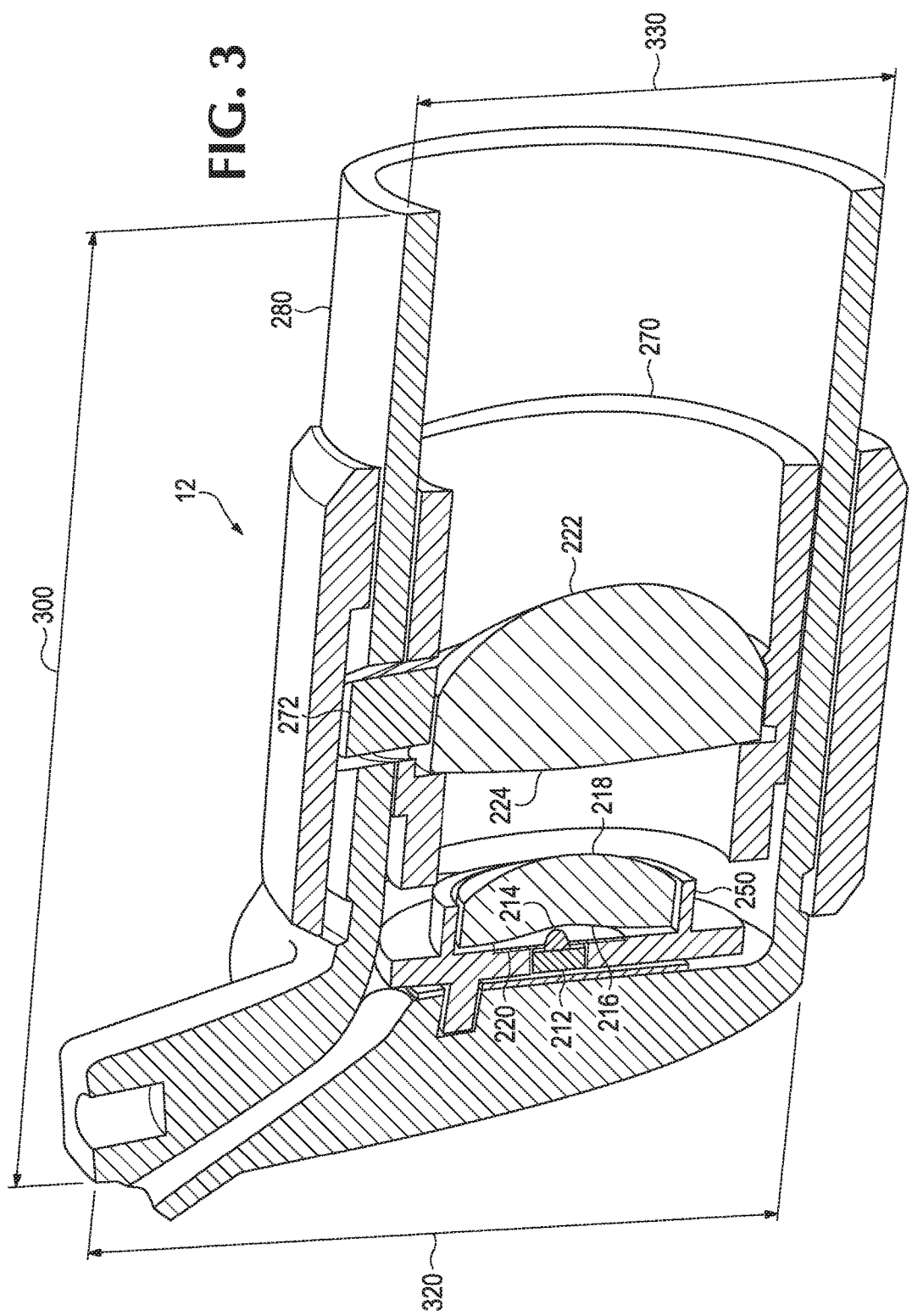
FIG. 3 is a cross-sectional view of a lamp for use in a medical headlamp assembly such as that of FIG. 1.
Figure 4:
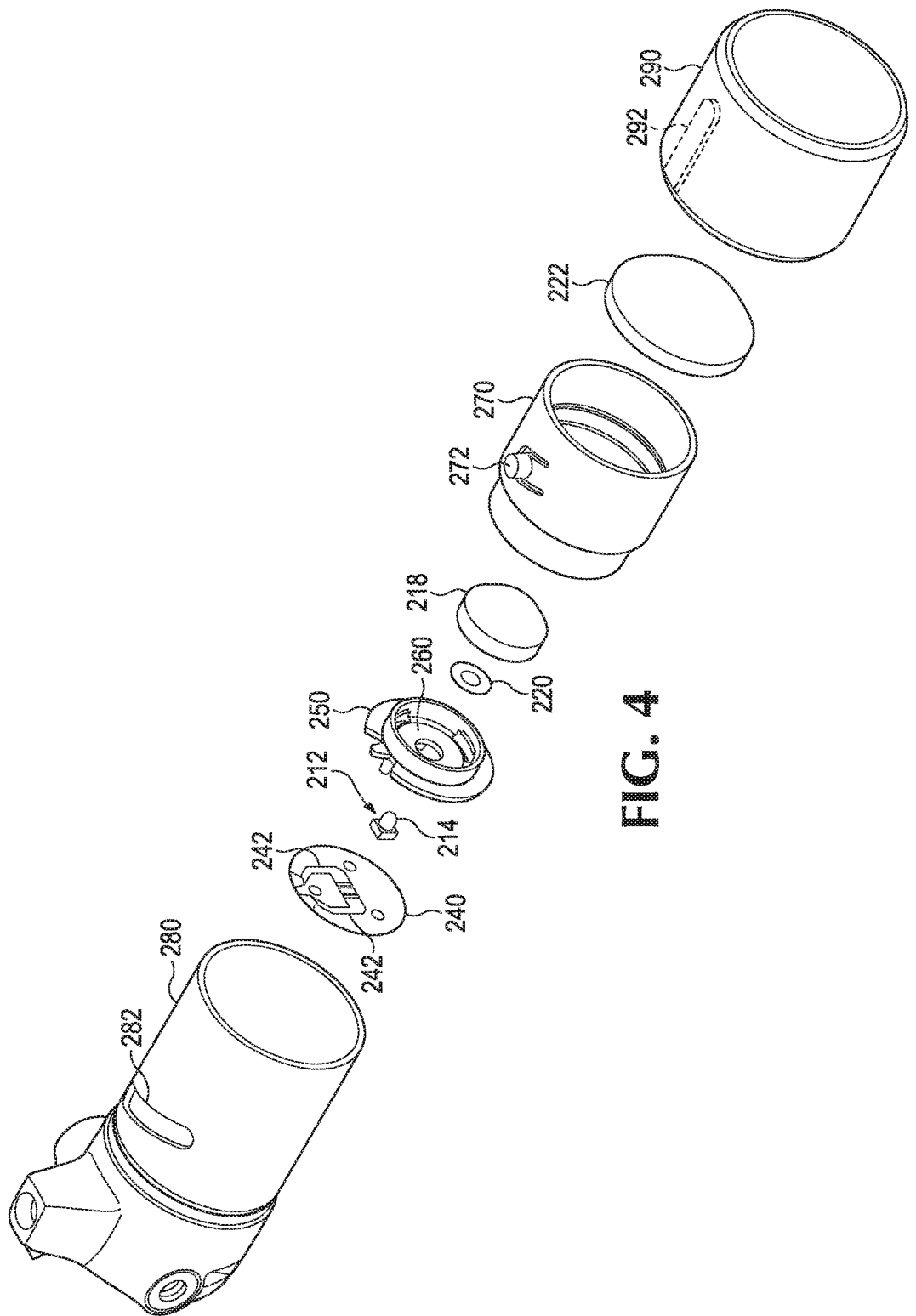
FIG. 4 is an exploded view of the lamp of FIG. 3.
Figure 6:
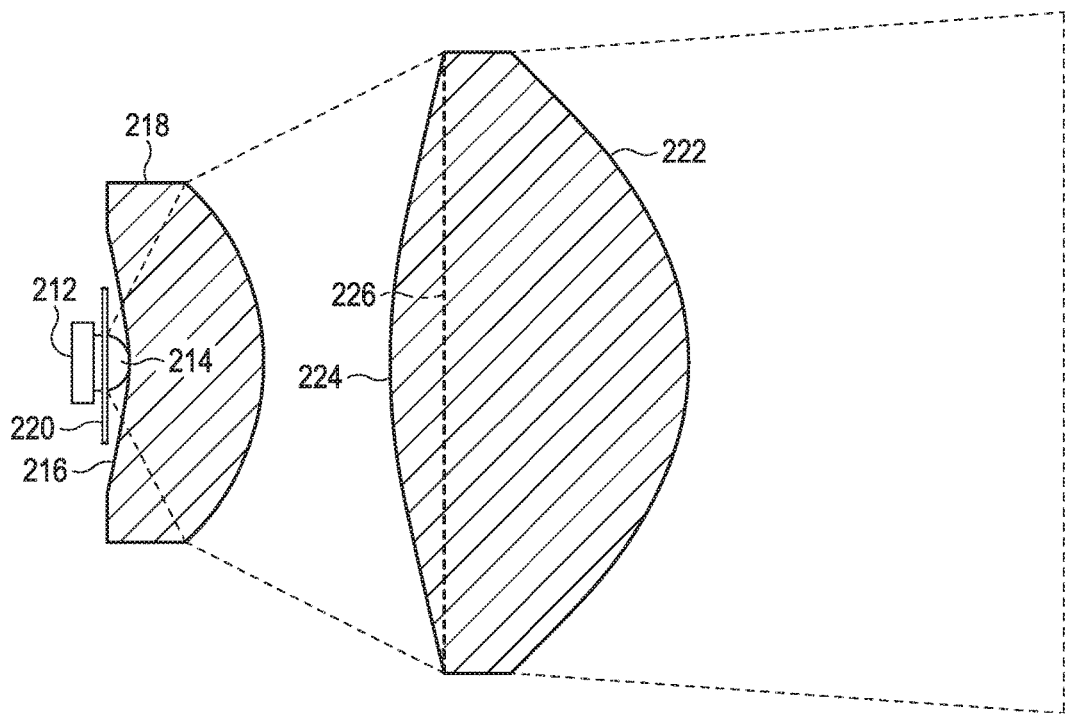
FIG. 6 is a diagram of the lamp of FIG. 3, showing the outer light rays when the system is in operation.
Figure 8:
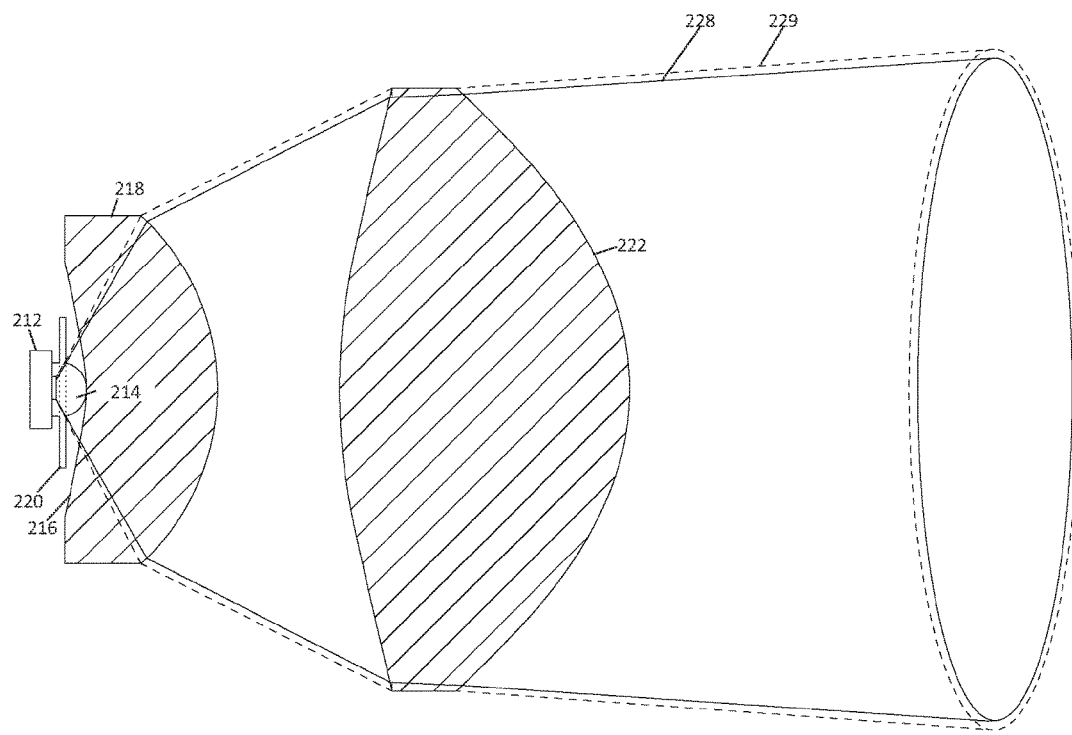
FIG. 8 is a diagram of the optical assembly of the headlamp of FIG. 1, showing the light beam in solid line, with the dimmer light that would extend outwardly if not blocked by the annular light block indicated by the region between the dashed line and the solid line.

Referring to FIGS. 3, 4 and 6, in a preferred embodiment, of an optical assembly 12, an LED assembly 212, including a domed silicone lens 214, and producing a light beam having a 3 dB beamwidth of 120°, has a 25μ (1 mil) thick annular light block 220 fitted around LED assembly 212, with the domed silicone lens 214 extending through the annulus of the light block 220. The beam exiting light block 220 has a beamwidth of 120° but with a much sharper edge then the beam from LED assembly 212. This phenomenon is illustrated in FIG. 8, where an actual beam, having a boundary 228 is missing a penumbral, dimmer portion, illustrated by the space between theoretical 25 penumbral boundary 229 (of the penumbra which would exist if not blocked by annular light block 220) and beam boundary 228. This contrasts with prior art systems in which an adjustable iris light block is placed entirely in front of the light source, resulting in a greater portion of the light being blocked and lost to beneficial use. Because this permits the use of the otherwise unusable 120° beam width assembly, this assembly permits a larger spot of light for the surgeon using the optical assembly 12. The placement of the light block 220 together with its 25μ thickness, creates a sharp boundary about the light, and ultimately creating a sharp spot of light, at the typical 80-100 mm (16-18 in) working distance. Lens 214 is fit into a concavity 216 formed in the back of an aspheric prime optic lens 218. Table 1 shows the LED assembly 212 characteristics for four differing embodiments. In an alternative preferred embodiment, an LED assembly is used that is similar to the Oslon Square LED assembly, but includes more than one LED die, and in another preferred embodiment more than one LED assembly is used.

In front of prime optic lens 218, an exit lens 222 has a convex rear surface 224, thereby better directing the captured light back to create a beam of constant illumination over area. The equation for the surface is:

$$Z=(CR^2)/(1+SQRT(1-(1+K)C^2R^2));$$

Where Z is the distance of the surface away from the apex of the rear surface 224 of the exit lens 222, in the longitudinal dimension, toward plane 226 (see FIG. 6), where:

R=radial distance from center in mm; and where C=0.05479 mm$^{-1}$, and K=−14.954 (unitless).

More generally, the curve described by the above equation has the characteristic that for every 0.5 mm chord connecting two points along the curve the perpendicular distance ("sagitta" or "sag") from the chord to the curve, at the chord midpoint, is at least 0.025 mm.

Figure 5:
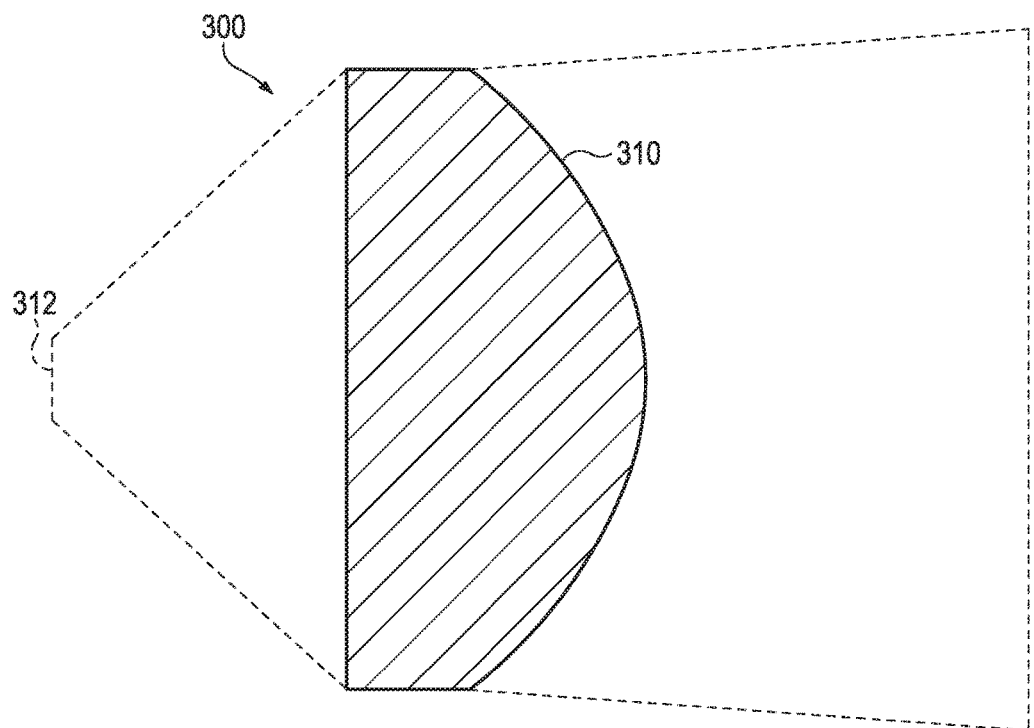
FIG. 5 is a diagram of the lens system of a prior art headlamp, showing the outer light rays when the system is in operation.

As noted in the background, prior art systems included an adjustable iris aperture in front of the light source to permit adjustment of light spot size and create a sharply defined edge and homogeneous brightness and color from edge to edge. Although this permitted flexibility with respect to spot size, the movable elements of the iris required the iris aperture to be positioned further in front, the light source resulting in more light being blocked. Also, the need to have moveable leaf elements that fit together could impart a noncircular shape to the beam and the spot of light produced by the beam. Even when an iris was not used, as illustrated by FIG. 5, prior art systems, such as optical arrangement 300, would lose light by placement of the prime lens 310 far ahead of the light source 312. By contrast, a preferred embodiment has a set aperture size created by the 25 micron-100 micron (1 to 4 mils) thick annular light block 220. This novel arrangement creates a far sharper light-spot boundary, due to the extremely thin circular aperture wall, resulting in virtually no light reflecting from the inner surface of annulus. This light block 220 is positioned around dome 214 of LED assembly 212, thereby blocking a smaller portion of the light produced by assembly 212.

The LED assembly 212 is driven by a 750 milliamp or greater current. A one (1) amp current at a typical battery voltage of 3.45 Volts results in a voltage drop through the LED assembly of about 3.15 Volts, due to some voltage drop through a rheostat, which is used to adjust light intensity, in the headstrap 16. This creates about 3.15 Watts of power that must be dissipated as heat from the LED assembly 212. The LED assembly 212 is driven by traces 242 that extend through a sheet of flex circuit 240 that is mounted behind prime lens holder 250 (FIGS. 3 and 4). Annular light block 220 fits into a round recess 260 in the center of holder 250. A layer of the flex circuit 240 is made of copper (except for channels where the copper has been removed to separate the traces 242 from the rest of the copper covering), which efficiently conducts heat away from assembly 212. Light is reflected from this conductive layer, which is close to the front, and at most covered with a transparent coating. This light is re-reflected back by the annular light block, preventing this yellowish light from entering the beam of light produced by assembly 10.

As illustrated in FIGS. 3 and 4, the exit lens 222 is held in a lens holder 270 that has a slot-follower 272 which is fitted into a curved slot 282 in an aft barrel 280. An outer ring 290 includes a straight internal longitudinal slot 292, and is mounted about aft barrel 280, so that when outer ring 290 is rotated, lens holder 270 is also rotated as slot-follower 272 is forced to stay in straight slot 292. This rotation forces slot-follower 272 to rotate within curved slot 282, which in turn causes slot-follower 272 and lens holder 270 to be moved either forward or backward in aft barrel 280. This either focuses or defocuses the light beam, creating a larger or smaller spot of light. The aft barrel 280 is made of aluminum and has a high thermal conductivity, whereas lens holder 270 and outer tube 290 are made of hard, black acrylonitrile butadiene styrene (ABS) polymer. Aft barrel 280 has a length 300 of 49.36 mm, and a height 320 of 38.61 mm. The front of aft barrel 280 has an outer diameter 330 of 27.26 mm. The other parts shown in FIGS. 3 and 4 are shown at the same scale as the aft barrel. The optical assembly 12 has a mass of 43 grams. The entire assembly 10, including batteries 18, has a mass of 340 grams.

TABLE 1

LED Assemblies Used in Various Embodiments

|  | Manufacturer Designation | Further Designation Class (Color) | LED Beam Angle |  |
|---|---|---|---|---|
| LED Assembly of Emb. 1 | Oslon Square | PC | 120 |  |
| LED Assembly of Emb. 2 | Oslon Square | EC | 120 |  |
| LED Assembly of Emb. 3 | Oslon Square | CC | 120 |  |
| LED Assembly of Emb. 4 | Oslon Square | EQW | 120 |  |
| Current Applied | 750 mA | 1 A | 1.2 A | 1.5 A |
| Lumen Output | | | | |
| LED Assembly of Emb. 1 | 252-346 | 312-429 | 372-511 | 408-561 |
| LED Assembly of Emb. 2 | 220-294 | 273-364 | 325-434 | 357-476 |
| LED Assembly of Emb. 3 | 189-271 | 234-336 | 279-401 | 306-440 |
| LED Assembly of Emb. 4 | 294-409 | 364-507 | 434-604 | 476-663 |
| Voltage | | | | |
| LED Assembly of Emb. 1 | 3.08 | 3.15 | 3.2 | 3.28 |
| LED Assembly of Emb. 2 | 3.08 | 3.15 | 3.2 | 3.28 |
| LED Assembly of Emb. 3 | 3.08 | 3.15 | 3.2 | 3.28 |
| LED Assembly of Emb. 4 | 3.08 | 3.15 | 3.2 | 3.28 |
| Wattage | | | | |
| LED Assembly of Emb. 1 | 2.31 | 3.15 | 3.84 | 4.92 |
| LED Assembly of Emb. 2 | 2.31 | 3.15 | 3.84 | 4.92 |
| LED Assembly of Emb. 3 | 2.31 | 3.15 | 3.84 | 4.92 |
| LED Assembly of Emb. 4 | 2.31 | 3.15 | 3.84 | 4.92 |
| Lm/Watt @ max lm | | | | |
| LED Assembly of Emb. 1 | 150 | 136 | 133 | 114 |
| LED Assembly of Emb. 2 | 127 | 116 | 113 | 97 |
| LED Assembly of Emb. 3 | 117 | 107 | 104 | 89 |
| LED Assembly of Emb. 4 | 177 | 161 | 157 | 135 |

Figure 7:
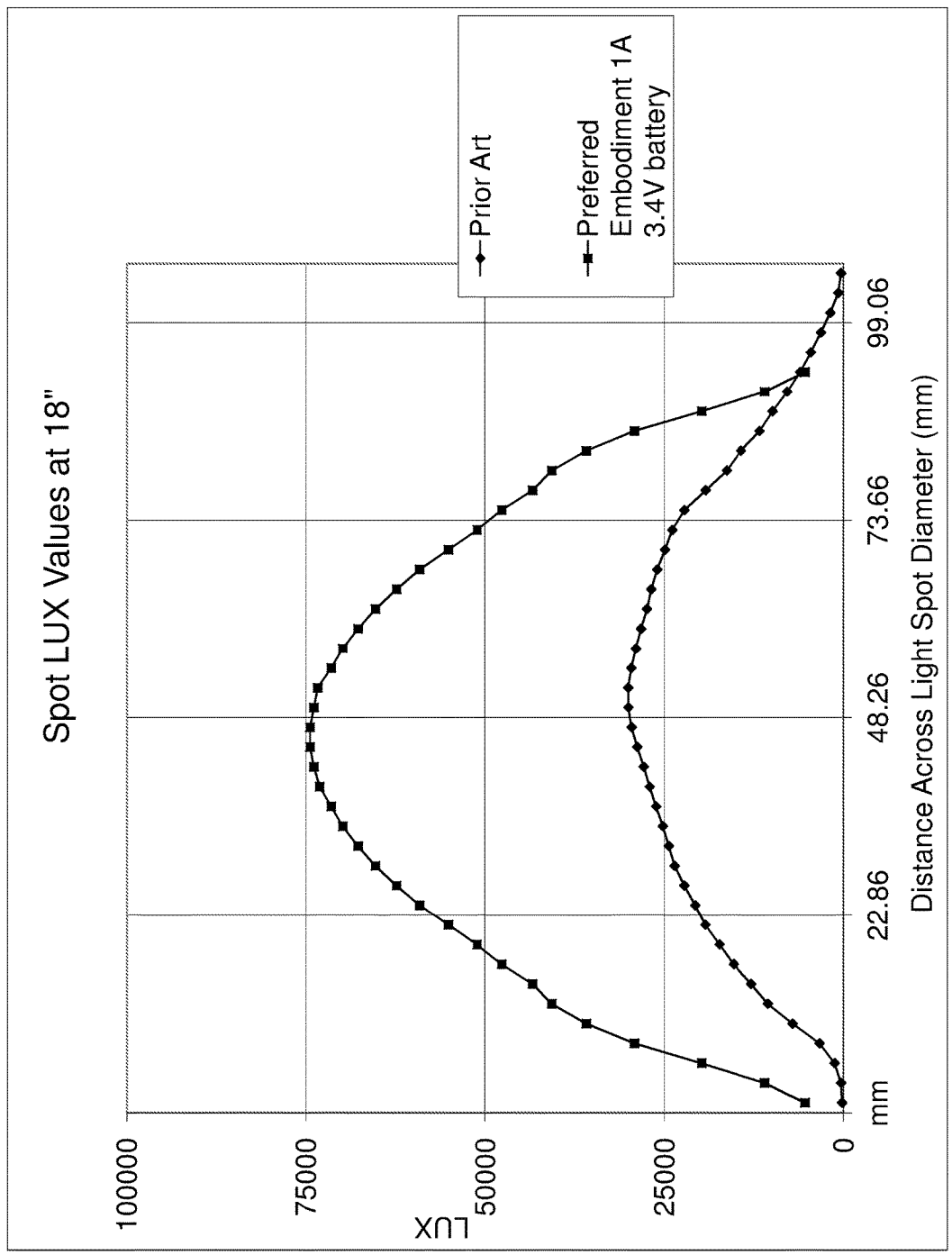
FIG. 7 is a graph of light intensity values from a spot formed on a white background formed 45.7 cm (18 inches) in front of the front surface of the headlamp, according to a preferred embodiment, using 1 Amp of current and a 3.4 Volt, from battery, voltage drop. The intensity values are taken along a diameter of the light spot.

The effect of the above detailed design is a medical headlamp assembly 10 with batteries 18 mounted on the headstrap assembly 16, and without a fan to provide forced air cooling, but which produces a brighter beam than previously available headlamp assemblies of this sort. The beam produced, in one preferred embodiment, has a light volume of 413 lumens with a color rendering index of at least 65. The beam is emitted relatively evenly from the 23 mm diameter front surfaces of the exit lens 222, and spreads out by 4.19 degrees in all directions as the beam advances. Referring to FIG. 7, a one (1) Amp lamp, as described above, where the voltage drop from the batteries is 3.4 Volts, produces a spot of light at 45.7 cm (18 inches) as shown. With a bright central area, about 52 mm wide at all above 50,000 lux at a color rendering index (CRI) of greater than 65. This is surrounded by a ring of about 10 mm width, where the light intensity declines from 50,000 lux to 25,000 lux. At the edges of the light beam, the brightness drops off by 20 dB in 0.5°. The lamp is operable in an ambient temperature of up to 30° Celsius, with no fan to cool the lamp.

This brightness is achieved by two improvements, with respect to prior art assemblies. First, the electric power applied to the LED assembly 212 is greater than in the prior art. Second, the proportion of light produced by the LED that is emitted in the beam is greater. The greater electric power of 2.5875 Watts creates a problem of successfully expressing the heat produced. It is highly advantageous to do this without the use of a fan, which would drive up electric power usage and create an unwanted noise. Accordingly, no fan is used in the preferred embodiment. The need to express the heat produced, is addressed by a longer aft barrel 280 which is made of aluminum and acts as a heat radiator, without blocking the surgeon's view. Also, the copper surface of flex circuit 240 conducts heat away from the LED assembly 212 and toward the bezel housing. A greater proportion of light produced by the LED is emitted in the light beam because: 1) the distance between the LED assembly 212 and the prime lens is shortened to virtually nothing, as the LED assembly 212 protrudes into a concavity 216 in the prime lens 218; 2) the adjustable iris, present in many prior art systems has been eliminated; 3) the annular light block 220 sits on the lens of the LED assembly 212, so that it is so far back that it blocks only a small proportion of the light. In one preferred embodiment 70% of the light produced by LED assembly 212 is emitted from the exit lens 222 as a light beam. Alternative preferred embodiments emit anywhere from 50% to 70% of the light produced by the led assembly 212 out of exit lens 222. This compares favorably with prior art systems where less than 45% of the light produced by the light source is emitted in the beam. In a preferred embodiment, the light beam produced from exit lens 222 has a volume of 114 to 161 lumens for every watt of power applied to LED assembly 212. In one alternative preferred embodiment, this figure ranges from 90 lumens of output light per watt to 161 lumens of output light per watt.

This device greatly eases the task of the surgeon, who may now have an adequately bright and wide spot for deep cavity surgery, without the need for the distracting noise and cumbersome extra weight of a fan and without the need of any power cable traversing from a sterile to a nonsterile zone.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A lamp having a front surface from which an output light beam having an output light beam width is emitted, comprising:
   (a) a high efficiency light source assembly producing a beam having a 3 dB beam width of greater than or equal to said output light beam width, said assembly having:
      (i) a substrate;
      (ii) a high efficiency light source supported by said substrate; and
      (iii) said high efficiency light source being contained in a lens in the form of a dome, positioned in front of and about said high efficiency light source and being supported by and joined to said substrate;
   (b) an optical assembly positioned to receive light from said high efficiency light source and produce a lamp light beam emitted from said front surface of said lamp;
   (c) a housing supporting said high-efficiency light source assembly and said optical assembly and an electrical conductor connected to said high-efficiency light source, for supplying electricity to said light source;
   (d) an annular light block, having a back, defining an annulus and placed on and about said lens, so that said lens protrudes through said annulus;
   (e) whereby some of said light emitted from said high energy light source, but at an angle outside of said output light beam width, strikes said back of said annular light block and is reflected back, away from said front surface, thereby creating a sharp boundary for said output light beam.

2. The lamp of claim 1, wherein said high efficiency light source is a light emitting diode.

3. The lamp of claim 1, wherein said lens is made of silicone.

4. The lamp of claim 1, wherein said annular light block is supported by said lens.

5. The lamp of claim 1, wherein said optical assembly includes a lens having a rear surface defining a concavity into which said light emitting diode assembly protrudes.

6. The lamp of claim 1, further having a mass of less than 30 grams.

7. The lamp of claim 1, that when said electrical conductor is connected to a one-amp current source, uses about 3.15 Watts of electricity and produces a beam of greater than 300 lumens from said front surface.

* * * * *